United States Patent [19]

Oda et al.

[11] Patent Number: 4,983,758

[45] Date of Patent: Jan. 8, 1991

[54] PROCESS FOR PRODUCING AN OPTICALLY ACTIVE ALPHA-ISOPROPYL-P-CHLOROPHENYLA-CETIC ACID

[75] Inventors: Yoshiaki Oda, Kashiwara; Takaharu Ikeda, Konan; Hiroshi Yamachika, Toyonaka, all of Japan

[73] Assignee: Sumitomo Chemical Company, Limited, Osaka, Japan

[21] Appl. No.: 279,095

[22] Filed: Dec. 2, 1988

[30] Foreign Application Priority Data

Dec. 3, 1987 [JP] Japan .................................. 62-306918
Dec. 8, 1987 [JP] Japan .................................. 62-311632
Dec. 11, 1987 [JP] Japan .................................. 62-314797
Jan. 22, 1988 [JP] Japan .................................. 63-13429
Jul. 26, 1988 [JP] Japan .................................. 63-187461

[51] Int. Cl.$^5$ .......................................... C07C 69/76
[52] U.S. Cl. ..................................... 560/105; 562/196
[58] Field of Search ........................ 560/105; 162/496

[56] References Cited

U.S. PATENT DOCUMENTS 4,277,494 7/1981 Faroog et al. .................... 560/105

FOREIGN PATENT DOCUMENTS 45-4511 11/1967 Japan .
50-25544 3/1975 Japan .
53-118411 10/1978 Japan .
57-171938 10/1982 Japan .
59-80627 5/1984 Japan .
61-103852 5/1986 Japan .

OTHER PUBLICATIONS

Chemical Abstract CA 110(15) 134950h 1988.
Chemical Abstract CA 110 (9) 74510c 1988.
Optical Resolution of 2-(4-Chlorophenyl)-3-Methyl-butanoic Acid by Preferential Crystallization with Achiral Amines by Hiroyuki Nohira, Daiyo Terunuma and Sinji Kobe pp. 1421 to 1423.
Isomerization-Crystallization Method in Optical Resolution by Kazutaka Arai, pp. 486 to 498.
Enantiomers, Racemates, and Resolutions, by J. Jacques et al. pp. 43 thru 89.
Optical Resolution of 2-(4-substituted Phenyl)-3-Methylbutanoic Acids with Diethylamine by Preferential Crystallization by Hiroyuki Nohira, Daiyo Terunuma, Shinzi Kobe, Ikuko Asakura, Akira Miyashita and Tasuku Ito Sep. 17, 1985; pp. 675 thru 681.

Primary Examiner—Paul J. Killos
Attorney, Agent, or Firm—Birch, Stewart, Kolasch & Birch

[57] ABSTRACT

A process for producing an optically active α-isopropyl-p-chlorophenylacetic acid (ICPA) of the formula:

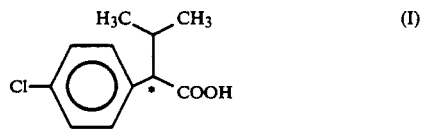

wherein the symbol * stands for an asymmetric carbon atom.

37 Claims, No Drawings

PROCESS FOR PRODUCING AN OPTICALLY ACTIVE ALPHA-ISOPROPYL-P-CHLOROPHENYLACETIC ACID

BACKGROUND OF THE INVENTION

1. Field of the Invention

The present invention relates to a process for producing an optically active α-isopropyl-p-chlorophenylacetic acid (hereinafter referred to as ICPA) of the formula:

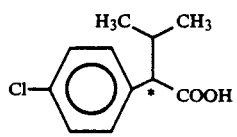

wherein the symbol * stands for an asymmetric carbon atom. An optically active ICPA, in particular (+)-ICPA, is useful as an acid component for producing pyrethroids, such as fenvarelate, used as effective insecticides (cf. Japanese Patent Kokai Publication No. 136245/1980).

2. Description of the Related Art

To produce an optically active ICPA, for example, the following methods comprising optical resolution are known:

(i) an optical resolution method wherein a diastereomer salt of ICPA with an optically active amine such as α-phenyl-β-(p-tolyl)-ethylamine or α-phenethylamine is subjected to crystallization (cf. Japanese Patent Kokai Publication Nos. 25544/1975 and 80627/1984), and (ii) an optical resolution method wherein a salt of ICPA with an achiral amine such as diethylamine is subjected to preferential crystallization (cf. Agric. Biol. Chem., 46, 1421 (1982)).

In such conventional methods, a desired optically active ICPA can be obtained by decomposing the salt of the optically active ICPA with an amine after the optical resolution.

After crystallizing off the desired ICPA salt, the mother liquor is rich in the corresponding ICPA salt having the opposite optical activity. Since the optically active ICPA salt dissolved in the mother liquor is usually useless, it is industrially significant to reuse the salt by racemization and another optical resolution.

However, according to the conventional methods, the optically active ICPA salt is racemized very slowly. Therefore, in order to convert an optically active ICPA salt into the form of racemic modification, it is necessary in practice to perform a complicated process comprising decomposing the salt to give the corresponding optically active ICPA (which is the undesired ICPA enantiomer), racemizing the free ICPA, forming a salt of the obtained racemic modification with an amine, and then optically resolving the salt. In addition, the resolving agent required to carry out the method (i) is expensive and should have a high optical purity in order to obtain ICPA in a highly optically pure form.

As mentioned above, the conventional methods for production of an optically active ICPA are unsatisfactory.

SUMMARY OF THE INVENTION

An object of the present invention is to provide a process for producing an optically active ICPA, in which, after optical resolution, the residual undesired optically active ICPA derivative can be easily racemized as such.

It has been found that, when a halo-substituted phenyl ester of ICPA is used in place of the conventional amine salts of ICPA, the undesired optically active ICPA ester remaining in the mother liquor after optical resolution can be directly racemized under a specific condition.

According to the present invention, there is provided a process for producing an optically active ICPA which comprises the following steps 1 through 4:

Step 1

ICPA or a halide thereof of the formula:

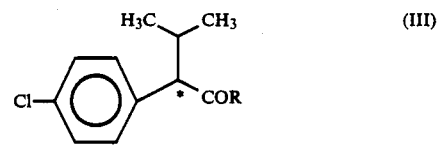

wherein R is a hydroxyl group or a halogen atom, and the symbol * stands for an asymmetric carbon atom, in the form of racemic modification is reacted with a halo-substituted phenol of the formula:

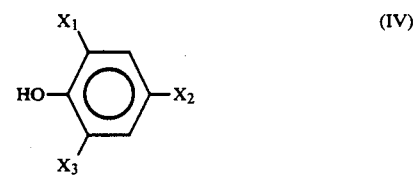

wherein $X_1$, $X_2$ and $X_3$ are independently halogen atoms, or two of them are independently halogen atoms and the rest is hydrogen atom or a lower alkyl group, to form an α-isopropyl-p-chlorophenylacetate (ICPA ester) of the formula:

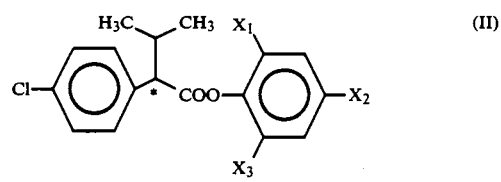

wherein $X_1$, $X_2$, $X_3$ and the meaning of the symbol * are the same as defined above, in the form of a racemic mixture.

Step 2

The ICPA ester in the form of the racemic mixture corresponding to the formula (II) is subjected to optical resolution by preferential crystallization from an organic solvent at a degree of supersaturation of not more than 150% at an intended crystallization temperature to separate off an optically active ICPA ester of the formula (II).

Step 3

The optically active ICPA ester obtained in the step 2 is subjected to hydrolysis while retaining its configuration to give the correspondingly optically active ICPA of the formula:

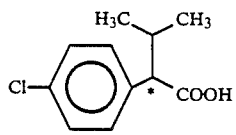

(I)

wherein the meaning of the symbol * is the same as defined above.

Step 4

The undesired optically active ICPA ester remaining in the mother liquor after the optical resolution in the step 2 is subjected to racemization by a strong organic base to form the racemic mixture of the ICPA ester, which can be subjected to another optical resolution according to the process of the step 2.

DETAILED DESCRIPTION OF THE INVENTION

An ICPA ester used in the present invention is not in the form of a racemate, but in the form of a racemic mixture.

Organic compounds having asymmetric centers can be classified into two groups, which are those of racemic modifications and of optically active compounds. The racemic modifications are in turn classified as racemates, racemic mixtures and racemic solid solutions. The possibility that a racemic modification is present as a racemic mixture is low, i.e. usually 5 to 10% [cf. J. Jacques, A. Collet, S. H. Wilen, "Enantiomers, Racemates, and Resolutions", John Wiley & Sons (1981), p 43 to 88].

Among the usual optical resolution methods such as a preferential crystallization method, a diastereomer salt method and an isomerization crystallization method, the preferential crystallization method is used in the present invention.

As the compound (III), which is one of the starting materials in the step 1, the racemic modification of ICPA or an acid halide thereof such as acid- chloride or bromide may be used. The ICPA halide is preferably used in view of its good reactivity.

ICPA is a known compound and commercially available. The ICPA halide can be prepared from ICPA according to a known general procedure, for example by reacting ICPA with a halogenating agent such as thionyl chloride in the presence of a catalyst such as γ-picoline in a suitable solvent such as benzene, toluene or n-hexane.

The other starting material in the step 1 is the halo-substituted phenol (IV) such as 2,4,6-trichlorophenol, 2,4,6-tribromophenol or 2,6-dichloro-p-cresol.

The esterification of the compound (III) with the compound (IV) may be carried out in a solvent in the presence or absence of a neutralizing agent. When the ICPA halide is used as the compound (III), the reaction in the step 1 is generally carried out in the presence of a neutralizing agent such as an organic base for example triethylamine, pyridine, tripropylamine, tributylamine, collidine or picoline, or an inorganic base for example sodium hydroxide, sodium carbonate, potassium hydroxide, potassium carbonate or lithium carbonate. The amount of such a neutralizing agent used may be 1 to 5 equivalents based on the ICPA halide.

The solvent used in the step 1 may be any solvent, provided it can dissolve the reacting substances without showing reactivity. Such a solvent is, for example, chloroform, methylene chloride, benzene, toluene, n-hexane, petroleum ether, ethyl ether, isopropyl ether, tetrahydrofuran, dioxane, acetone, methyl ethyl ketone, dimethylformamide or dimethylsulfoxide. Although the amount of such a solvent used is not restricted, it is usually 1 to 10 times by weight the amount of the compound (III).

When a mixture of the above-mentioned organic solvent such as toluene or tetrahydrofuran with water is used as the solvent, the esterification in the step 1 may be carried out in the presence of a catalyst such as a quaternary ammonium salt, for example benzyltriethylammonium chloride or tetra-n-butylammonium chloride. Such a catalyst is usually used in an amount of 0.1 to 20% by mole based on the amount of the halo-substituted phenol (IV).

The reaction temperature in the step 1 is in the range of from −20° to +100° C., preferably from 0° to 50° C.

After the reaction, by evaporating off the solvent from the reaction mixture and optionally purifying the residue by for example recrystallization, the ICPA ester (II) in the form of racemic mixture can be obtained in a high yield.

The ICPA esters of the formula (II), both in the form of racemic mixture and in an optically resolved form, are novel compounds.

In the step 2, the optically active ICPA ester of the formula (II) can be obtained by subjecting the product of the step 1 to optical resolution. According to the present invention, the optical resolution is carried out by preferential crystallization from an organic solvent under such a condition that the solvent is supersaturated with the product of the step 1 at a degree of supersaturation of not more than 150% at an intended crystallization temperature.

Such an organic solvent used in the step 2 is not particularly restricted and for example an aromatic hydrocarbon such as benzene or toluene, an aliphatic hydrocarbon such as pentane, hexane, heptane, cyclohexane or petroleum ether, a halogenated hydrocarbon such as methylene chloride, chloroform, carbon tetrachloride or chlorobenzene, an ether such as ethyl ether, isopropyl ether, tetrahydrofuran or dioxane, an aprotic polar solvent such as acetone, methyl ethyl ketone, N,N-dimethylformamide or dimethylsulfoxide, an alcohol such as methanol, ethanol, n-propanol or isopropanol, an ester such as ethyl acetate, or a mixture thereof.

In the context of the present invention, the term of "supersaturation" is intended to mean a state that a solute, which is the ICPA ester, is present in a solvent in an amount of more than the amount required to form a saturated solution at a certain temperature, the whole quantity of the solute being not always dissolved in the solvent.

In this connection, the term of a "degree of supersaturation" means a ratio of the amount of a solute present in a supersaturated solution of the invention to the amount of the solute required for saturation at a certain temperature. Thus, for example at the "degree of supersaturation of 150%", a solute is present in a solvent in the amount of 1.5 times by weight the amount required for saturation.

In the step 2 according to the present invention, the ICPA ester (II) in the form of racemic mixture is added to the organic solvent in such an amount that the solvent is supersaturated with the ester (II) at a degree of supersaturation of not more than 150% at an intended crystallization temperature. Then, the mixture of the ester and the solvent is heated to form a solution. By cooling the solution to a crystallization temperature and/or concentrating the solution, the desired optically active ester (II) can be crystallized.

When the degree of supersaturation at an intended crystallization temperature is excessively high, since both the desired and the undesired enantiomers may be simultaneously crystallized, the optical purity of the obtained crystalline may be deteriorated. Therefore, it is preferred to prepare a supersaturated solution at a degree of supersaturation of not more than 150%, in particular not more than 145% at an intended crystallization temperature. Although the lower limit of the degree of supersaturation is not restricted, it is preferably at least 110%. A lower degree may result in a deteriorated rate of crystallization.

The crystallization temperature may vary with the particular condition.

When the ester (II) subjected to the crystallization is more or less optically active, i.e. the content of one enantiomer is more or less higher than that of the other enantiomer in the ester, the optically active ester of higher content is spontaneously preferentially crystallized after allowing to stand, cooling or concentrating the supersaturated solution.

However, in most cases, the ester (II) subjected to the crystallization is in the form of racemic mixture. Since the solution of the ester (II) may remain in the state of supersaturation in the usual sense even after cooling to an intended crystallization temperature, the crystallization of the desired optically active ester (II) may be induced by seeding a crystal of the corresponding optically active ester.

The amount and particle size of the seed crystal are not restricted. A size-reduced crystal is preferably seeded in an amount in the range of from 1 to 10% by weight based on the amount of the ICPA ester in the solution.

An optically active ICPA ester used as the seed crystal can be prepared by halogenating the correspondingly optically active ICPA, esterifying the ICPA halide with the halo-substituted phenol (IV) and then recrystallizing the obtained optically active ICPA ester from hexane.

The optically active ICPA ester thus obtained in the step 2 may be optionally purified by for example recrystallization.

In the step 3 of the present method, the optically active ICPA ester (II) obtained in the step 2 is hydrolysed with retaining the configuration to give the desired correspondingly optically active ICPA (I).

The hydrolysis is carried out in the presence of an acid, in particular an inorganic acid such as sulfuric acid, hydrochloric acid, hydrobromic acid or nitric acid, such an acid being used as a 10 to 50% by weight aqueous solution.

The water required for the hydrolysis can be supplied from the above-mentioned aqueous solution of the acid. The amount of water used is not less than the equimolar amount based on the amount of the optically active ICPA ester. The upper limit of the amount of water is not restricted.

An organic solvent may be present in this step, unless it influences the hydrolysis.

The hydrolysis temperature may be in the range of from 20° C. to the boiling temperature of the reaction solution.

Thus, the optically active ICPA (I) can be obtained from the correspondingly optically active ICPA ester.

After preferentially crystallizing off the optically active ICPA ester in the step 2, the mother liquor is rich in the ICPA ester having the opposite optical activity. In the step 4, the undesired optically active ICPA ester can be easily racemized as such with using a racemizing agent, for example an organic strong base such as 1,8-diazabicyclo[5.4.0]undec-7-ene (DBU), 1,5-diazabicyclo[4.3.0]non-5-ene (DBN) or 1,4-diazabicyclo[2.2.2]octane (DBO).

According to the present invention, the mother liquor containing the undesired optically active ICPA ester may be usually directly subjected to racemization. However, it is also possible to separate off the ICPA ester from the mother liquor and then racemize the ester dissolved in a suitable organic solvent.

The concentration of the racemizing agent may vary with the type of the racemizing agent used. In general, the the concentration of the racemizing agent is, the faster the racemization proceeds. However, when the concentration of the racemizing agent is excessively high, side reactions may occur. For example, the concentration of DBU is preferably in the range of from 1 to 5% by weight.

Similarly, although the higher the racemizing temperature is, the faster the racemization proceeds, an excessively high temperature may lead to side reactions. Therefore, the racemization is preferably carried out at a temperature of not higher than the boiling point of the reaction solution.

The ICPA ester in the form of racemic mixture obtained in the step 4 can be subjected to the process of the step 2.

As mentioned above, in the process according to the present invention, by esterifying the racemic modification of ICPA or the halide thereof and subjecting the ester to preferential crystallization, the optically active ICPA ester having a desired configuration can be obtained. Then, the optically active ICPA ester is subjected to hydrolysis to give the desired optically active ICPA.

It is commercially advantageous that, according to the present invention, the ester of the undesired optically active ICPA which remains in the mother liquor after crystallizing off the desired optically active ICPA ester can be subjected to racemization as such to form racemic mixture which in turn may be subjected to optical resolution.

Thus, the present invention is characterized by the use of the ICPA ester (II), the racemic mixture of which can be subjected to preferential crystallization and also which in an optically resolved form can be directly racemized. Examples of preferred ICPA esters of the present invention are, for example, 2,4,6-tribromophenyl ester, 2,4,6-trichlorophenyl ester and 2,6-dichlorolo-p-tolyl ester.

PREFERRED EMBODIMENTS OF THE INVENTION

EXAMPLE 1

To a solution of ICPA (91.9 g) in toluene (160 ml), γ-picoline (48 μl) was added. To the solution, thionyl chloride (38 ml) was dropwise added at 40° C. over five minutes and then stirred for three hours at the same temperature.

After completion of the reaction, the reaction mixture was cooled, and washed with water, 10% sodium carbonate solution and then water. The organic phase was dried over anhydrous magnesium sulfate. After the solvent was distilled off under vacuum, α-isopropyl-p-chlorophenylacetyl chloride (ICPA chloride) was obtained as a pale yellow oil.

The obtained ICPA chloride was dissolved in chloroform (300 ml). The solution was dropwise added to a solution of 2,4,6-tribromophenol (143 g) and triethylamine (43.8 g) in chloroform (1200 ml) at room temperature over 30 minutes and then stirred for one hour.

After the reaction was completed, the reaction mixture was washed with water, saturated sodium hydrogen carbonate and then water. After the organic phase was dried over anhydrous magnesium sulfate, the solvent was distilled off under vacuum.

The oily residue was crystallized from hexane. The crude crystalline was recrystallized from hexane to give colorless crystalline 2,4,6-tribromophenyl ICPA ester (yield 195 g, 85.5%).
m.p. 106°–107° C.
$^1$H-NMR (CDCl$_3$): δ=0.75 (d, 3H, J=6 Hz), 1.15 (d, 3H, J=6 Hz), 1.9–2.8 (m, 1H), 3.45 (d, 1H, J=10 Hz), 7.4 (s, 4H), 7.6 (s, 2H)
IR (CHCl$_3$) 1760 cm$^{-1}$ The obtained 2,4,6-tribromophenyl ICPA ester (1.88 g) was dissolved in hexane (40 ml) while heating. Then, the solution was cooled to 25° C. and seeded with crystalline 2,4,6-tribromophenyl (+)-ICPA ester (188 mg). After allowing to stand for one hour at 25° C., a crystal formed was filtered off and dried under vacuum to give 2,4,6-tribromophenyl (+)-ICPA ester (251 mg).
m.p. 133°–134° C.
$[α]_D^{25}$ = +76.2° (c=1.16, hexane), 88.8% ee The seed crystal used was beforehand prepared by acid chlorinating (+)-ICPA, esterifying the chloride with 2,4,6-tribromophenol and recrystallizing the ester from hexane three times.
m.p. 136°–136.5° C.
$[α]_D^{25}$ = +77.6° (c=0.559, chloroform), 100% ee After the crystal of the (+)-ICPA ester was filtered off, the filtrate was subjected to racemization by adding DBU (0.82 g) and heating the mixture to 50° C. for three hours. Then, the mixture was cooled, washed with 2N-HCl and then water. Then, the organic phase was dried over anhydrous magnesium sulfate. After magnesium sulfate was filtered off, the solvent was distilled off to give 2,4,6-tribromophenyl (±)-ICPA ester (1.70 g).
m.p. 106°–107° C.
$[α]_D^{25}$ = +0.0° (c=1.03, hexane)

By subjecting the product obtained by the racemization to the above-mentioned optical resolution, further 303 mg of 2,4,6-tribromophenyl (+)-ICPA ester was obtained.

The (+)-ICPA ester (500 mg) in 6N-HCl (8 ml) was refluxed for one hour. The reaction mixture was cooled to room temperature, extracted with toluene and washed with water. The organic phase was extracted with 0.1N sodium hydroxide (8 ml). The alkaline aqueous phase was acidified to pH 2 with 6N-HCl and extracted with toluene. The toluene was washed with water and concentrated under vacuum to give (+)-ICPA (yield 182.2 mg, 90.1%).
$[α]_D^{25}$ = +42.7° (c=1.01, CHCl$_3$), 90% ee

EXAMPLE 2

With using 2,4,6-trichlorophenol in place of 2,4,6-tribromophenol, ICPA was esterified and post-treated in the same manner as in Example 1 to obtain 2,4,6-trichlorophenyl ICPA ester.
Yield 71.8%
m.p. 79°–80° C.
$^1$H-NMR (CDCl$_3$): δ=0.75 (d, 3H, J=6 Hz), 1.15 (d, 3H, J=6 Hz), 2.1–2.8 (m, 1H), 3.45 (d, 1H, J=10 Hz), 7.3 (s, 6H)
IR (CHCl$_3$): 1760 cm$^{-1}$ The obtained 2,4,6-trichlorophenyl ICPA ester (9.64 g) was dissolved in hexane (50 ml) while heating. Then, the solution was cooled to 25° C. and seeded with crystalline 2,4,6-trichlorophenyl (+)-ICPA ester (964 mg). After allowing to stand at 25° C., a crystal formed was filtered off and dried under vacuum to give 2,4,6-trichlorophenyl (+)-ICPA ester (1.97 g).
m.p. 103°–104° C.
$[α]_D^{25}$ = +90.9° (c=1.10, hexane), 91.8% ee The seed crystal used was prepared in the same manner as in Example 1 except that 2,4,6-trichlorophenol was used in place of 2,4,6-tribromophenol.
m.p. 105°–105.5° C. $[α]_D^{25}$ = +84.4° (c=1.03, chloroform), 100% ee Then, the (+)-ICPA ester (250 mg) was subjected to hydrolysis in the same way as in Example 1 and purified by recrystallization from hexane to give (+)-ICPA (yield 91.1 %).
$[α]_D^{25}$ = +44.0° (c=1.01, CHCl$_3$)

EXAMPLE 3

With using 2,6-dichlorop-cresol in place of 2,4,6-tribromophenol, ICPA was esterified and aftertreated in the same manner as in Example 1 to obtain 2,6-dichloro-p-tolyl ICPA ester.
Yield 58.7%
m.p. 66° C.
$^1$H-NMR (CDCl$_3$): δ=0.75 (d, 3H, J=6 Hz), 1.15 (d, 3H, J=6 Hz), 2.0–2.7 (m, 1H), 2.25 (s, 3H), 3.5 (d, 1H, J=10 Hz), 7.1 (s, 2H), 7.3 (s, 4H)
IR (CHCl$_3$): 1750 cm$^{-1}$ The obtained 2,6-dichloro-p-tolyl ICPA ester (11.2 g) was dissolved in hexane (50 ml) while heating. Then, the solution was cooled to 25° C. and seeded with crystalline 2,6-dichloro-p-tolyl (+)-ICPA ester (1.0 g). After allowing to stand at 25° C., a crystal formed was filtered off and dried under vacuum to give 2,6-dichloro-p-tolyl (+)-ICPA ester (2.0 g).
$[α]_D^{25}$ = +90.0° (c=1.04, hexane)

The seed crystal used was prepared in the same manner as in Example 1 except that 2,6-dichloro-p-cresol was used in place of 2,4,6-tribromophenol.
m.p. 92.5°–93° C.
$[α]_D^{25}$ = +91.5° (c=1.04, hexane), 100% ee Then, by subjecting the (+)-ICPA ester (1.8 g) to hydrolysis in the same manner as in Example 1, (+)-ICPA (yield 0.93 g, 90%) was obtained.
$[α]_D^{25}$ = +44.0° (c=1.01, CHCl$_3$)

EXAMPLE 4

After crystallization according to Example 2, the filtrate was subjected to racemization by adding DBN (1.5 g) and heating the mixture to 80° C. for 150 minutes. Then, the mixture was cooled to room temperature, and washed with 2N-HCl and then water. The organic phase was dried over anhydrous magnesium sulfate. After magnesium sulfate was filtered off, the solvent was distilled off under vacuum to give 2,4,6-trichlorophenyl (±)-ICPA ester (yield 8.61 g).

$[\alpha]_D^{25} = +0.0°$ (c=1.00, hexane)

EXAMPLE 5

To a solution of 2,6-dichloro-p-tolyl (+)-ICPA ester (0.500 g; $[\alpha]_D^{25} = +90.0°$ (c=1.00, hexane), 100% ee) in chloroform (6.0 ml), DBO (0.28 g) was added and heated to 40° C. for 150 minutes. Then, the mixture was cooled, and washed with 2N-HCl and then water. The organic phase was dried over anhydrous magnesium sulfate. After magnesium sulfate was filtered off, the solvent was distilled off under vacuum to give 2,6-dichloro-p-tolyl (±)-ICPA ester (yield 0.495 g).

$[\alpha]_D^{25} = -0.1°$ (c=1.00, hexane)

What is claimed is:

1. An optically active α-isopropyl-p-chlorophenylacetate of the formula:

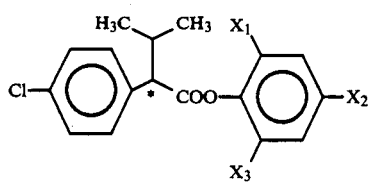

wherein $X_1$, $X_2$ and $X_3$ are independently halogen atoms, or two of them are independently halogen atoms and the third is a hydrogen atom or a lower alkyl group, and the symbol * stands for an asymmetric carbon atom.

2. A process for producing an optically active α-isopropyl-p-chlorophenylacetate of the formula:

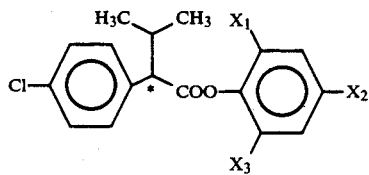

wherein $X_1$, $X_2$ and $X_3$ are independently halogen atoms, or two of them are independently halogen atoms and the third is a hydrogen atom or a lower alkyl group, and the symbol * stands for an asymmetric carbon atom, which comprises subjecting the corresponding α-isopropyl-p-chlorophenylacetate in the form of racemic mixture to optical resolution by preferential crystallization from an organic solvent supersaturated with the racemic mixture at a degree of supersaturation of not more than 150% by weight at an intended crystallization temperature.

3. The process according to claim 2, wherein the whole quantity of the racemic mixture in the supersaturated solution is not dissolved in the solvent.

4. The process according to claim 3, wherein a desired optically active α-isopropyl-p-chlorophenylacetate of the formula (II) is preferentially crystallized, the other optically active ester of the formula (II) remaining in the mother liquor.

5. An α-isopropyl-p-chlorophenylacetate in the form of racemic mixture corresponding to the formula:

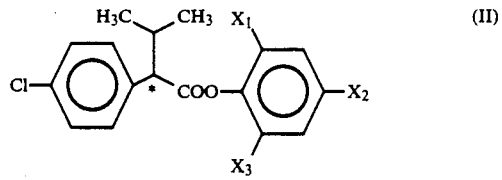

wherein $X_1$, $X_2$ and $X_3$ are independently halogen atoms, or two of them are independently halogen atoms and the third is a hydrogen atom or a lower alkyl group, and the symbol * stands for an asymmetric carbon atom.

6. A process for producing an α-isopropyl-p-chlorophenylacetate in the form of racemic mixture corresponding to the formula:

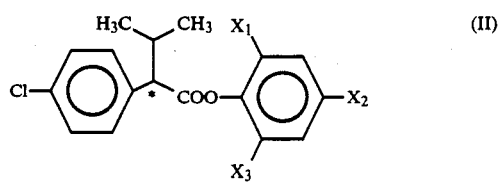

wherein $X_1$, $X_2$ and $X_3$ are independently halogen atoms, or two of them are independently halogen atoms and the rest is a hydrogen atom or a lower alkyl group, and the symbol * stands for an asymmetric carbon atom, wherein α-isopropyl-p-chlorophenylacetic acid or a halide thereof of the formula:

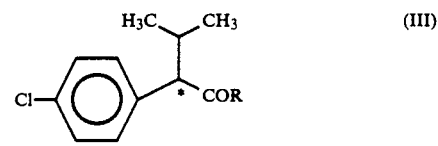

wherein R is a hydroxyl group or a halogen atom, and the meaning of the symbol * is the same as defined above, in the form of racemic modification is reacted in a solvent in the presence or absence of a neutralizing agent with a halo-substituted phenol of the formula:

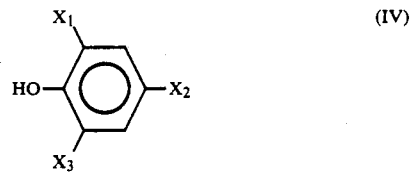

wherein $X_1$, $X_2$ and $X_3$ are the same as defined above.

7. The process according to claim 6, wherein the α-isopropyl-p-chlorophenylacetyl halide of the formula (III) is reacted in the presence of the neutralizing agent.

8. The process according to claim 7, wherein the neutralizing agent is an organic base.

9. The process according to claim 7, wherein the neutralizing agent is an inorganic base.

10. A process for producing an α-isopropyl-p-chlorophenylacetate in the form of racemic mixture corresponding to the formula:

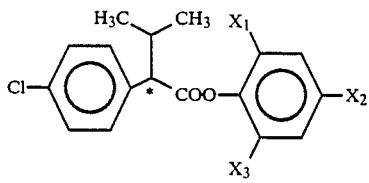

(II)

wherein $X_1$, $X_2$ and $X_3$ are independently halogen atoms, or two of them are independently halogen atoms and the third is a hydrogen atom or a lower alkyl group, and the symbol * stands for an asymmetric carbon atom, wherein an optically active corresponding α-isopropyl-p-chlorophenylacetate of the formula (II) is directly subjected to racemization.

11. The process according to claim 10, wherein the corresponding α-isopropyl-p-chlorophenylacetate in the form of a racemic mixture is subjected to optical resolution by preferential crystallization from an organic solvent supersaturated with the racemic mixture at a degree of supersaturation of not more than 150% by weight at an intended crystallization temperature and the desired optically active acetate of formula (II) is preferentially crystallized so that the other optically active ester of the formula (II) remains in the mother liquor, wherein the optically active α-isopropyl-p-cholorophenylacetate remaining in the mother liquor is subjected to racemization.

12. The process according to claim 11, wherein the racemization is carried out in the presence of a strong organic base.

13. The process according to claim 12, wherein the strong organic base is 1,8-diazabicyclo undec-7-ene, 1,5-diazabicyclo[4.4.0]non-5-ene or 1,4-diazabicyclo[2.2.2]octane.

14. The process according to claim 13, wherein the amount of the strong organic base is in the range of from 0.1 to 10 mole % based on the amount of the optically active ester subjected to racemization.

15. The process according to claim 14, wherein the racemization is carried out in an organic solvent.

16. The process according to claim 15 wherein the amount of the organic solvent is in the range of from 20 to 100 times by weight the amount of the strong organic base.

17. The process according to claim 7, wherein the isopropyl-p-chlorophenylacetyl halide of the formula (III) is an acid chloride.

18. The process according to claim 7, wherein the isopropyl-p-chlorophenylacetyl halide of the formula (III) is an acid bromide.

19. The process according to claim 6, wherein the halosubstituted phenol of the formula (IV) is a member selected from the group consisting of 2,4,6-trichlorophenol, 2,4,6-tribromophenol and 2,6-dichloro-p-cresol.

20. The process according to claim 8, wherein the neutralizing agent is an organic base selected from the group consisting of triethylamine, pyridine, tripropylamine, tributylamine, collidine and picoline, and wherein the organic base is present in an amount of from 1 to 5 equivalents based on the halide of formula (III).

21. The process according to claim 9, wherein the neutralizing agent is an inorganic base selected from the group consisting of sodium hydroxide, sodium carbonate, potassium hydroxide, potassium carbonate and lithium carbonate, and wherein the inorganic base is present in an amount of from 1 to 5 equivalents based on the halide of formula (III).

22. The process according to claim 6, wherein the solvent is present in an amount of from 1 to 10 times by weight of the amount of the compound of formula (III).

23. The process according to claim 22, wherein the solvent is a mixture of (1) water and (2) toluene or tetrahydrofuran and a catalyst is present in an amount of from 0.1 to 20 percent by mole based on the halo-substituted phenol of formula (IV).

24. The process according to claim 23, wherein the catalyst is a quaternary ammonium salt selected from the group consisting of benzyltriethyammonium chloride and tetra-n-butylammonium chloride.

25. The process according to claim 6, wherein the reaction temperature is from 0° to 50° C.

26. The process according to claim 6, wherein $X_1$, $X_2$ and $X_3$ are (1) all bromide atoms, (2) all chloride atoms or (3) two of them are chloride atoms and the third a methyl group.

27. The optically active acetate of formula (II) according to claim 1, wherein $X_1$, $X_2$ and $X_3$ are all bromide atoms.

28. The optically active acetate of formula (II) according to claim 1, wherein $X_1$, $X_2$ and $X_3$ are all chloride atoms.

29. The optically active acetate of formula (II) according to claim 1, wherein two of $X_1$, $X_2$ and $X_3$ are chloride atoms and the third is a methyl group.

30. The racemic mixture of acetate of formula (II) according to claim 5, wherein $X_1$, $X_2$ and $X_3$ are all bromide atoms.

31. The optically active acetate of formula (II) according to claim 5, wherein $X_1$, $X_2$ and $X_3$ are all chloride atoms.

32. The optically active acetate of formula (II) according to claim 5, wherein two of $X_1$, $X_2$ and $X_3$ are chloride atoms and the third is a methyl group.

33. The process according to claim 2, wherein $X_1$, $X_2$ and $X_3$ are (1) all bromide atoms, (2) all chloride atoms or (3) two of them are chloride atoms and the third a methyl group.

34. The process according to claim 2, wherein the degree of supersaturation is from 110% to 145% by weight at an intended crystallization temperature.

35. The process according to claim 2, wherein the organic solvent is a member selected from the group consisting of benzene, toluene, pentane, hexane, heptane, cyclohexane, petroleum ether, methylene chloride, chloroform, carbon tetrachloride, chlorobenzene, ethyl ether, isopropyl ether, tetrahydrofuran, dioxane, acetone, methyl ethyl ketone, N,N-dimethylformamide, dimethylsulfoxide, methanol, ethanol, n-propanol, isopropanol, ethyl acetate, and a mixture thereof.

36. The process according to claim 2, wherein crystallization is induced by seeding the supersaturated racemic mixture with a crystal of the desired optically active acetate of formula (II), wherein the crystal is present in an amount of from 1 to 10% by weight based on the acetate of formula (II).

37. The process according to claim 13, wherein the amount of the strong organic base is in the range of from 1 to 5% by weight based on the amount of the optically active ester subjected to racemization.

* * * * *